(12) United States Patent
Aubele et al.

(10) Patent No.: US 7,426,855 B2
(45) Date of Patent: Sep. 23, 2008

(54) METHOD AND APPARATUS FOR TESTING THE ADHESIVE STRENGTH OF OVERLAYS OF PLAIN BEARING BUSHINGS

(75) Inventors: Thomas Aubele, Undenheim (DE); Gerhard Weil, Hunfelden (DE); Maik Wilhelm, Ober-Olm (DE)

(73) Assignee: Federal Megal Wiesbaden GmbH + Co. KG, Wiesbaden (DE)

( * ) Notice: Subject to any disclaimer, the term of this patent is extended or adjusted under 35 U.S.C. 154(b) by 135 days.

(21) Appl. No.: 11/377,039

(22) Filed: Mar. 16, 2006

(65) Prior Publication Data
US 2006/0243046 A1 Nov. 2, 2006

(30) Foreign Application Priority Data
Mar. 16, 2005 (DE) .................. 10 2005 013 204

(51) Int. Cl.
G01N 19/04 (2006.01)
(52) U.S. Cl. .............................. 73/150 A; 73/9; 73/10; 73/46; 73/49.8; 73/53.05; 73/865.9
(58) Field of Classification Search .............. 73/9, 73/10, 46, 49.8, 53.05, 150 A, 865.9
See application file for complete search history.

(56) References Cited

U.S. PATENT DOCUMENTS

| 4,000,656 | A |   | 1/1977  | Moioli       |         |
|-----------|---|---|---------|--------------|---------|
| 4,862,738 | A | * | 9/1989  | Jankowski    | 73/118.1 |
| 5,072,611 | A | * | 12/1991 | Budd et al.  | 73/118.1 |
| 5,226,308 | A | * | 7/1993  | Gibson       | 73/9    |
| 5,239,864 | A |   | 8/1993  | von Pragenau |         |

(Continued)

FOREIGN PATENT DOCUMENTS

DE   1 054 743   9/1959

(Continued)

OTHER PUBLICATIONS

Baudry G et al, "Fatigue Property Evaluationof Bearing Steels Issued From Rotary Continuous Casting", Cahiers D'Informations Techniques de la Revue de Metallurgie, Oct. 1, 1992.

Primary Examiner—Edward Lefkowitz
Assistant Examiner—Freddie Kirkland, III
(74) Attorney, Agent, or Firm—Robert L. Stearns; Dickinson Wright PLLC

(57) ABSTRACT

A method and an apparatus for testing the adhesive strength of overlays attached to the inside of plain bearing bushings. The method is characterized in specifying clearance between the plain bearing bushing tested and a rotating or oscillating pin extending through the bushing. Next, feeding a liquid medium into the gap between the bushing and the pin and oscillating the plain bearing bushing and pin relative to one another perpendicularly to the bushing axis for a given period and examining the bushing after the load test. The corresponding apparatus comprises a pin mounted rotatably in a pin receptacle and on which there is arranged a first drive mechanism. In addition, a bushing receptacle is provided, in which the plain bearing bushing is fitted, wherein the pin is mounted with predetermined clearance in the bushing. The apparatus additionally comprises a mechanism for bringing about oscillating relative movement of bushing receptacle and pin receptacle.

21 Claims, 3 Drawing Sheets

U.S. PATENT DOCUMENTS

| | | | | |
|---|---|---|---|---|
| 5,372,033 A | * | 12/1994 | Jackson et al. | 73/53.05 |
| 6,802,203 B1 | * | 10/2004 | Averill et al. | 73/9 |
| 6,840,082 B2 | * | 1/2005 | Evans | 73/9 |

FOREIGN PATENT DOCUMENTS

| | | |
|---|---|---|
| DE | 22 61 789 C3 | 10/1979 |
| DE | 28 40 425 C3 | 8/1981 |
| DE | 32 00 439 A1 | 7/1983 |
| DE | 44 10 639 A1 | 9/1995 |
| DE | 196 50 616 C2 | 9/2001 |
| DE | 101 59 949 C1 | 5/2003 |

* cited by examiner

METHOD AND APPARATUS FOR TESTING THE ADHESIVE STRENGTH OF OVERLAYS OF PLAIN BEARING BUSHINGS

This application claims priority to German Patent Application No. 10 2005 013 204.9, filed Mar. 16, 2005.

BACKGROUND

1. Field of the Invention

The invention relates to a method for testing the adhesive strength of overlays attached to the inside of plain bearing bushings. The invention also relates to an apparatus for testing said adhesive strength.

2. Related Art

Plain bearing bushings generally comprise a steel backing and an overlay, which may consist of a plastics material or a metal alloy. A sintered layer, which may consist of sintered bronze for example, is often arranged between the overlay and the steel backing. It is such plain bearing bushings which the method according to the invention is designed to test.

Plain bearing bushings serve, as a rule, for mounting rotating shafts, wherein the lubricant is moved in the circumferential direction in the lubricant gap. Hydrodynamic lubrication is thus produced.

However, there are also applications in which the lubricant flows at the same time in the axial direction, which may lead to flow erosion in the overlay and optionally in the layers therebelow. This flow erosion may lead to detachment of the overlay and thus to failure of the bearing bushing.

Such flow conditions prevail, for example, in diesel injection pumps, in which the diesel fuel assumes the function of the lubricant. The bushings serve therein in particular for mounting eccentric shafts, with the consequence that the bearing bushings are periodically also loaded in a radial direction, such that high axial flow velocities may arise in the then widening lubrication gap. The higher the flow velocity, the greater the risk of flow erosion.

As a result of the flow, the overlay is exposed to high shear stress. It is therefore desirable to simulate this shear stress under different conditions and to test the adhesive strength of the overlay.

The only test methods and apparatuses which are known are those with which test the tensile strength of layers of a flat composite material.

A test method is known from EP 0 212 694 which determines the adhesion of an overlay to a bronze layer of a flat multilayer plain bearing material using a testing apparatus according to ISO 4624. In this method the roughened flat end face of a testing bar of the testing apparatus is adhered to the overlay.

This method is complex and does not provide any information 25 about the resistance of the overlay to shear stress, which is caused inter alia by flow of a liquid medium.

Depending on the field of use, the plain bearing bushing is also subjected to axial load, in this case generally abruptly or in pulsed manner, wherein the shaft extending through the bushing in each case undergoes bending, leading on the one hand to edge pressure, loading of the bushing edge, and on the other hand to abrupt inflow of the liquid medium into the gap opening up between shaft and bushing.

DE-PS 22 61 789 discloses a machine component with a 5 coating for preventing chemical wear. A bearing testing machine is described for testing purposes which is equipped with a test shaft, an interchangeable steel bushing being attached thereto with sliding fit. Two connecting rod bearings with connecting rod are positioned on the steel or test bushing. To prevent the test bushing from rotating relative to the test shaft, the bushing is additionally secured by a tongue-and-groove arrangement. Interchangeable unbalanced flywheels may be used to subject the tight-fitting test bushing to a larger or smaller degree of vibration by means of the rotating test shaft. This patent specification does not provide any information about testing the adhesive strength of overlays attached to the inside of plain bearing bushings using purposeful application and inflow of a liquid medium.

DE 28 40 425 C3 also merely describes a plain bearing test rig in which, for the tests, in each case individual plain bearing halves are mounted in the lower part of the bearing receptacle. To establish test conditions, static load is applied just to the upper, untreated plain bearing half. A relatively large bearing clearance in the plain bearing half to be tested is additionally used to ensure that the journal does not come into mechanical contact with the test shell on start-up. Once the test conditions have been set, the plain bearing half to be tested is subjected to static load by means of a continuously adjustable hydraulic cylinder by changing the loading direction by means of a lever arm on the bearing receptacle.

It is therefore an object of the invention to provide a method and an apparatus with which the adhesive strength of overlays of plain bearing bushings under shock load may be tested simply.

SUMMARY

One object is achieved by the following steps:

specifying clearance between the plain bearing bushing to be tested and extending an either stationary or rotating and/or oscillating pin through the bushing, feeding a liquid medium into the gap between the plain bearing bushing and the pin, oscillating the plain bearing bushing and pin relative to one another perpendicularly to the bushing axis for a given period with a given force, and examining the plain bearing bushing after the load test for damage to the overlay.

The method makes it possible to test the adhesive strength of the overlay in the particularly heavily stressed edge area of the plain bearing bushing. The oscillating force perpendicular to the bushing axis bends the pin, such that it alternately rests against the bushing edges and opens up a gap at the bushing edges, into which the liquid medium flows abruptly. The bushing edges are thereby exposed to permanent alternating stress comprising radial load, load relief and flow load caused by the liquid medium in the axial direction. If adhesive strength of the overlay is ensured in these areas, then adhesive strength is also provided in the other areas of the plain bearing bushing. This method simulates extreme loading of plain bearing bushings, as occurs for example in diesel injection pumps.

The force is selected in accordance with the purpose to which the plain bearing bushing is to be used. For example, the procedure may begin with a low force, which may then be increased in stages, wherein the plain bearing bushing is optionally removed between test phases and examined. In this way, a maximum admissible load may be determined, at which the overlay does not become detached. This method is preferably performed within the force range from 2 kN to 60 kN, in particular from 10 to 50 kN, particularly preferably in the range from 20 to 40 kN.

The force is preferably exerted sinusoidally, which most closely reproduces the most common conditions of use.

The clearance may also be simply adjusted by providing pins with different external diameters for the plain bearing bushing to be investigated. The clearance is preferably set in the range from 30 pm to 500 pm for plain bearing bushings with external diameters from 10 to 30 mm. Preferred values within this clearance range are 30 pm to 300 pm and 30 pm to 100 pm.

The length of the plain bearing bushings to be tested is in the range, for example, from 10 to 30 mm.

The pin may be arranged in stationary manner, but it is preferable for the pin to perform oscillating rotation at a frequency of 5 to 15 Hz. Preferred frequencies are 8 to 12 Hz, in particular 9 to 10 Hz. In the case of oscillating rotation of the pin, movement preferably takes place over an angle of up to 20°, in particular up to 15°.

Instead of oscillating rotation, continuous rotation is also possible, wherein 5 revolutions per minute to 15 revolutions per minute are preferred.

The investigations may be performed using liquid media of different viscosities. Preferably, liquid media are used with viscosities of 0.2 to 8 mPa preferably 1 to 5 mPas, wherein these values relate to a temperature of 100° C.

A preferred temperature range for performing testing of the plain bearing bushing is between 20° C. and 250° C., preferably in the range from 100° C. to 150° C.

It has been demonstrated that, depending on bushing size, overlay material, viscosity of the liquid medium, clearance and temperature, 10 to 60 minutes is sufficient for a test phase. Further preferred durations are 20 to 50 minutes, 25 to 35 minutes, particularly preferably 30 minutes.

Hydraulic oil, engine oil, diesel fuel or diesel oil substitute are used as the liquid media.

With regard to the apparatus, the object is achieved with an apparatus comprising the following components:

pin, which is mounted rotatably in a pin receptacle and on which there is arranged a first drive mechanism or means, a bushing receptacle, in which the plain bearing bushing to be tested may be interference-fitted, wherein the pin is mounted with predetermined clearance in the plain bearing bushing, a mechanism or means for bringing about oscillating relative movement of bushing receptacle and pin receptacle, and a mechanism or means for feeding a liquid medium into the gap between pin and plain bearing bushing.

The relative movement may be brought about in various ways.

According to a first embodiment, the pin receptacle is arranged in stationary manner and the bushing receptacle is connected with a second drive mechanism or means for bringing about the oscillating movement.

This means that the load is exerted by means of the movement of the bushing receptacle. Because the pin receptacle is arranged stationarily, the pin is caused to bend by the load via the bushing. The oscillating movement is preferably performed with simultaneous rotation or oscillating rotation of the pin.

According to a second embodiment, the bushing receptacle is arranged in stationary manner and the pin receptacle is connected with a second drive mechanism or means for bringing about the oscillating movement.

This second drive means may be a force cylinder, for example, which acts on the bushing receptacle or on the pin receptacle and brings about oscillating movement, which results in axial loading of the bushing and thus in deformation of the pin.

In order to bring about deformation or bending of the pin in a simple manner, the pin is of hollow construction. This makes the pin more resilient. Different degrees of bending of the pin may be achieved with the same load by means of different wall thicknesses of the tubular pin. It is thus straightforwardly possible to set different method conditions with the same loads by using interchangeable pins with different wall thicknesses.

In order to be able to measure the force acting on the bushing, the respectively stationary receptacle is preferably equipped with a force gauge or a force gauge is arranged on the stationary receptacle.

BRIEF DESCRIPTION OF THE DRAWINGS

Exemplary embodiments of the invention are explained in more detail below with reference to the drawings, in which.

DETAILED DESCRIPTION

Figure 1:
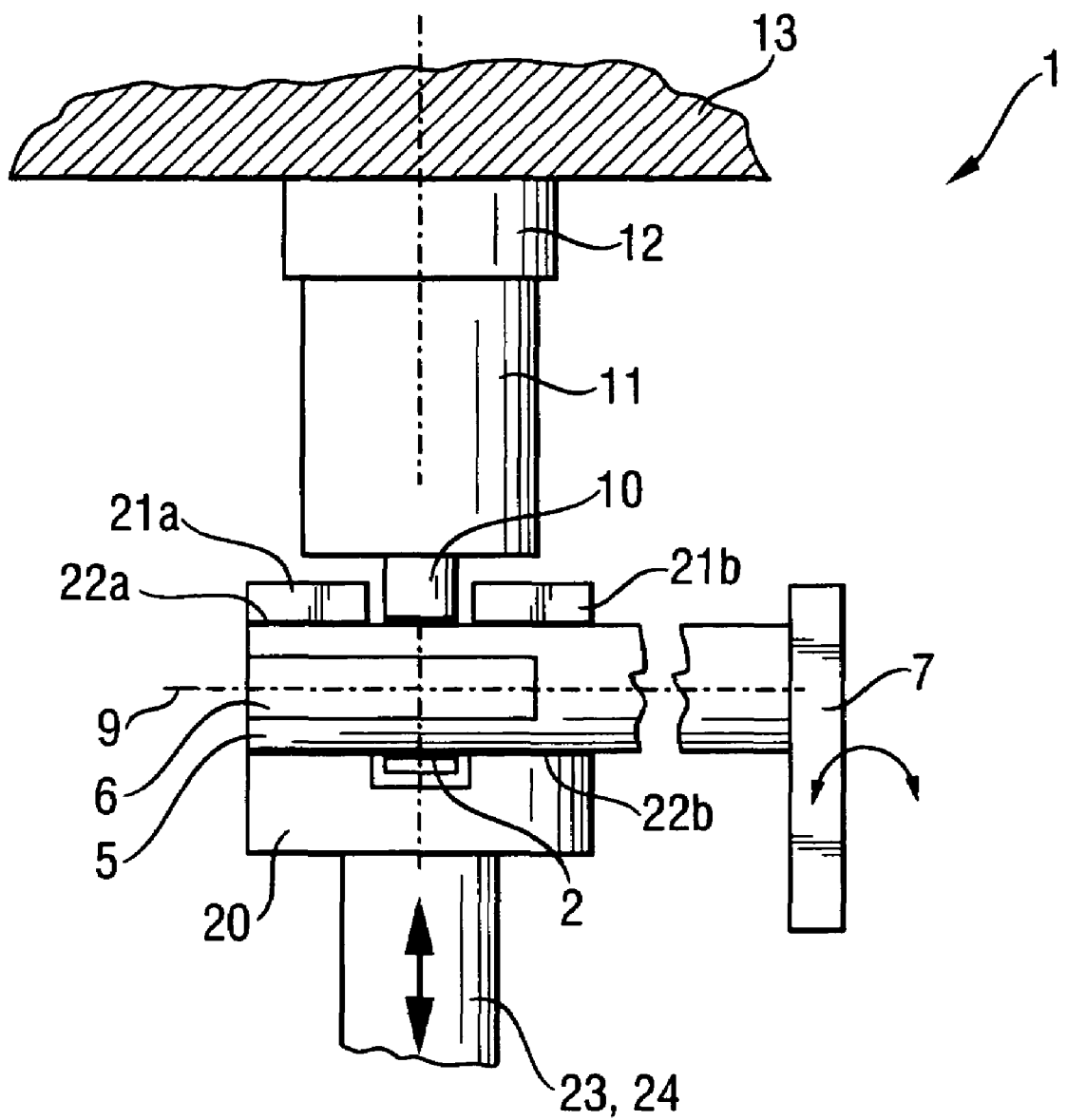
FIG. 1 is a schematic representation of a first embodiment of the apparatus.

FIG. 1 shows an apparatus 1 comprising a stationary crossbeam 13, on the underside of which there are arranged a force gauge 12, a connecting element 11 and a bushing receptacle 10. A bushing 2 to be tested is fitted, preferably with an interference fit, in the bushing receptacle 10.

A pin 5 comprising a cavity 6 extends through the bushing 52. The cavity 6 extends from the left-hand end of the pin to beyond the area of the bushing to be tested. The pin 5 is mounted in a bushing receptacle 20 of U-shaped construction. The bearings 22a, b of the pin 5 are located in a pair of arms 21a and 21b, which project perpendicularly upwards. The bearings 22a, b allow rotational movement of the pin 5. To this end, the pin is connected at the right-hand end with a first drive mechanism or means 7. This drive means 7 is so designed that the pin performs a rotational movement, which may also be oscillatory.

The pin receptacle 20 is provided at the lower end with a second drive mechanism or means 23, which takes the form of a force cylinder 24. This force cylinder 24 performs a raising and lowering movement, indicated by the arrows, such that the pin 5 may be moved in oscillatory manner in the bushing to be tested perpendicularly to a central axis 9 of the bushing 2. Since the bushing 2 is arranged stationarily, this results in bending of the pin 5, as is explained with reference to FIG. 3.

Figure 2:
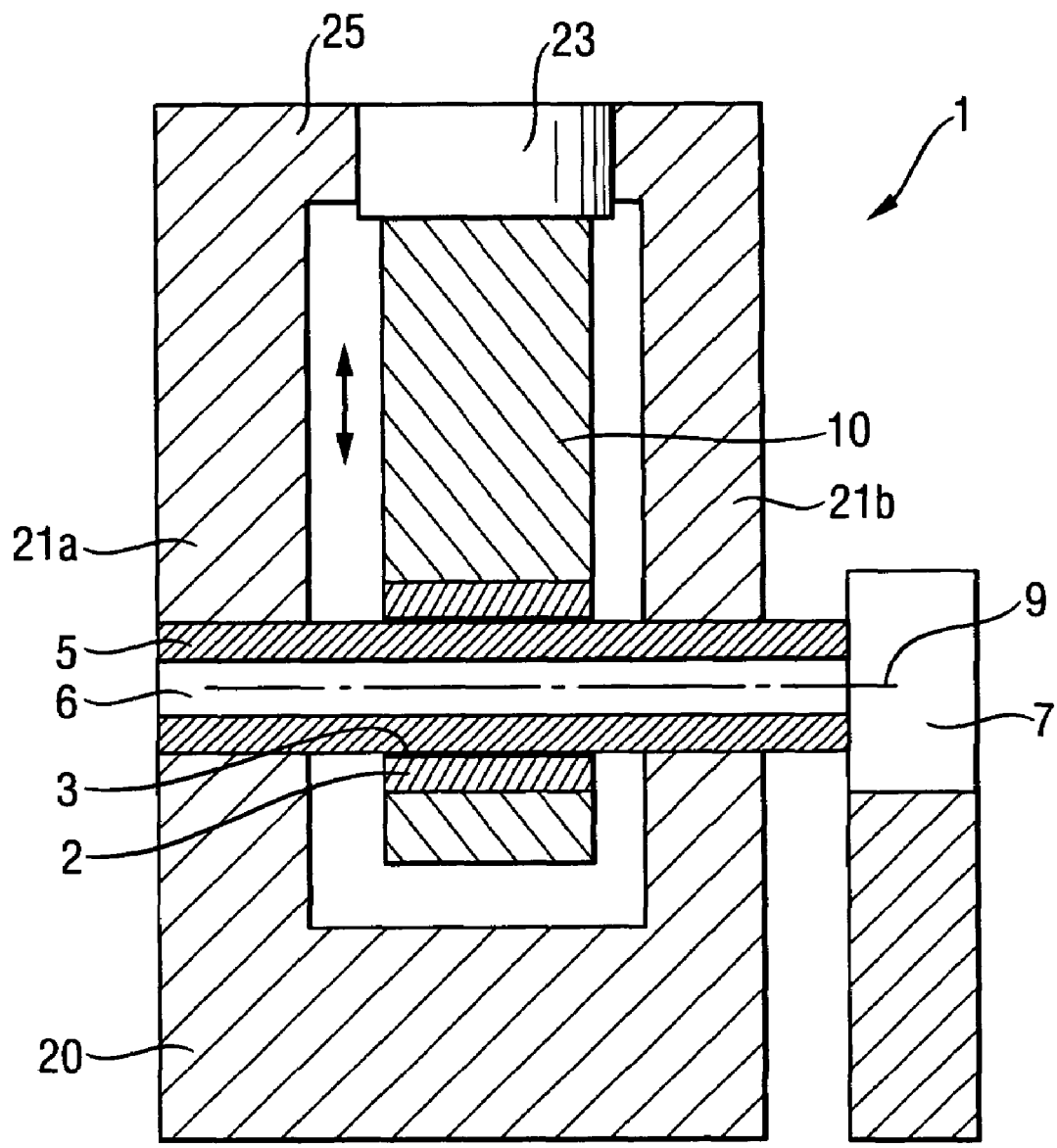
FIG. 2 is a schematic representation of a second embodiment of the apparatus.

FIG. 2 shows a further embodiment of the apparatus 1. This embodiment differs from the embodiment shown in FIG. 1 in that the pin receptacle 20 is of stationary construction and the bushing receptacle 10 is connected with a second drive mechanism or means 23, which is located in the crossbeam 25 of the pin receptacle 20. This second drive means 23 may also take the form of a force cylinder, which moves the bushing receptacle 10 up and down in oscillating manner and thus forces the plain bearing bushing 2 against the stationarily arranged pin 5 perpendicularly to the axis 9 of the plain bearing bushing. The term stationary, when used in relation to the pin 5, means that the pin 5 is fixed with regard to vertical movements and can only perform rotational movements. To this end, the pin is connected to a first drive mechanism or means 7 at the right-hand end. In the embodiment illustrated here, the pin 5 takes the form of a tube with the cavity 6.

Figure 3:
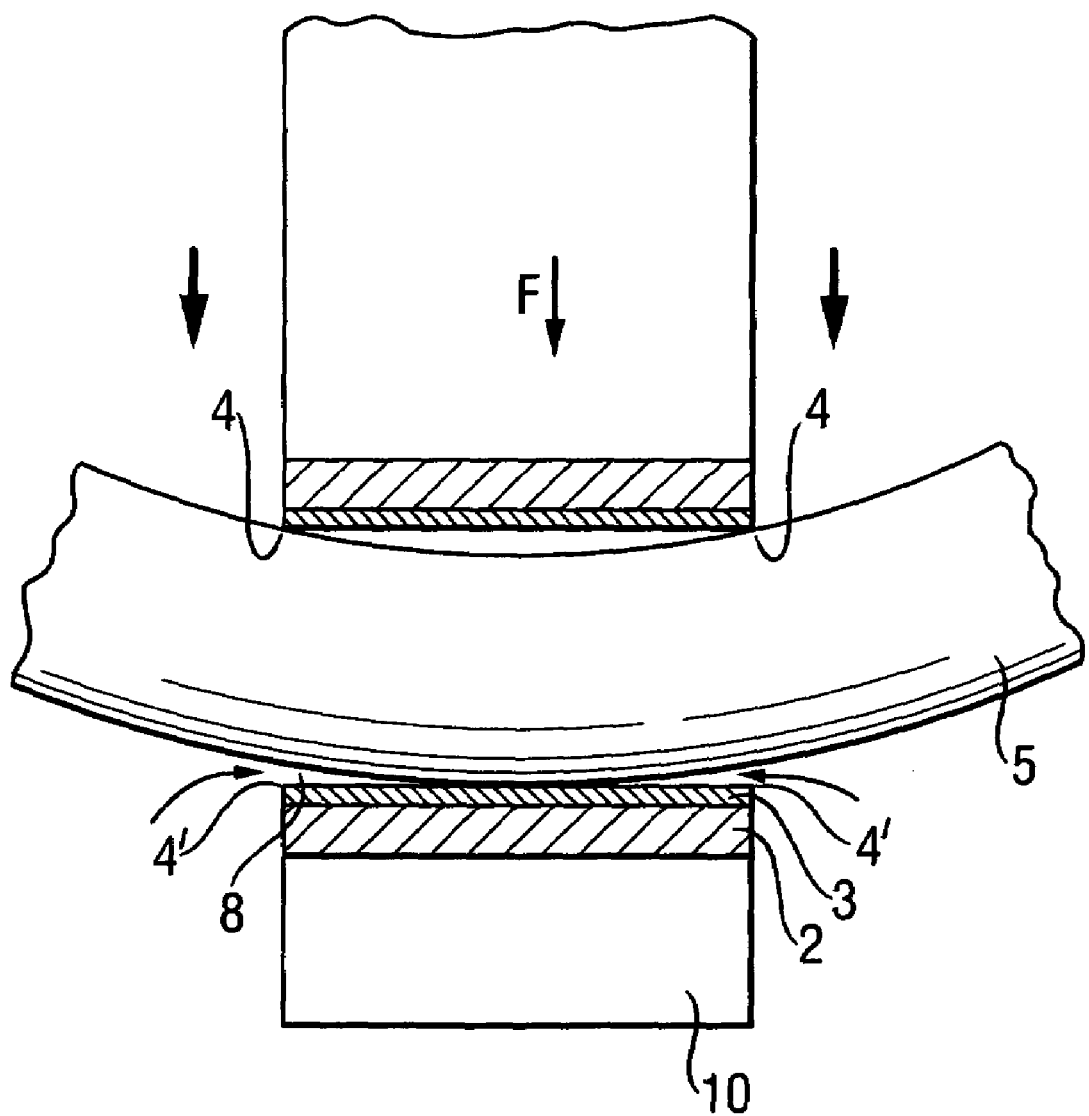
FIG. 3 is an enlarged representation of plain bearing bushing and pin under

FIG. 3 shows a bushing 2 with an overlay 3, which is arranged in a bushing receptacle 10. The bushing receptacle 10 is moved downwards in the position illustrated in FIG. 3, such that the pin 5 is bent downwards. The bend is exaggerated in FIG. 3, to show that the plain bearing bushing rests against the pin 5 at the bushing edges 4, wherein a gap 8 opens up between the pin 5 and the overlay 3 at the bottom, such that the liquid medium, as indicated by the arrows, may flow into the gap. The liquid medium is preferably not supplied at elevated pressure, but merely at gravitational pressure.

If the bushing receptacle 10 is moved upwards, the gap 8 is closed and the pin is bent upwards, with the consequence that the pin rests against the lower bushing edges 4'. The liquid medium in the gap 8 is forced abruptly out of the gap 8. At the same time, a corresponding gap is formed in the upper area at the edges 4, into which the liquid medium flows abruptly.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

The invention claimed is:

1. A method for testing the adhesive strength of overlays attached to the inside of plain bearing bushings, having the following steps:
    specifying clearance between the plain bearing bushing to be tested and an either stationary or rotating and/or oscillating pin extending through the plain bearing bushing,
    feeding a liquid medium into the gap between the plain bearing bushing and the pin,
    oscillating the plain bearing bushing and pin relative to one another perpendicularly to the bushing axis for a given period with a given force bending the pin, such that it alternately rests against edges of the bushing and opens up said gap, into which the liquid medium flows abruptly, and
    examining the plain bearing bushing after the load test for damage to the overlay.

2. The method according to claim 1, wherein a clearance of from 30 pm to 500 pm is established for plain bearing bushings with external diameters of from 10 to 30 mm.

3. The method according to claim 1, wherein plain bearing bushings with a bushing length of from 10 to 30 mm are tested.

4. The method according to claim 1, wherein the given force amounts to 2 kN to 60 kN.

5. The method according to claim 1, wherein the given force is exerted sinusoidally.

6. The method according to claim 1, wherein the pin performs oscillating rotation at a frequency of from 5 to 15 Hz.

7. The method according to claim 6, wherein the pin performs oscillating rotation over an angle of up to +20°.

8. The method according to claim 1, wherein liquid media with viscosities of 0.2 to 8 mPas are used, wherein these viscosity values relate to a temperature of 100° C.

9. The method according to claim 1, wherein liquid media in the temperature range of from 20° C. to 250° C. are used.

10. The method according to claim 1, wherein the given period amounts to 10 to 60 minutes, in particular 20 to 50 minutes.

11. The method according to claim 1, wherein hydraulic oil, engine oil, diesel fuel or diesel oil substitute are used as the liquid media.

12. The method according to claim 1, wherein the oscillating step is performed by holding the plain bearing stationary and oscillating the pin perpendicular to the bushing axis.

13. The method according to claim 1, further including feeding the liquid medium into the gap by introducing the liquid medium into the gap externally from the pin.

14. An apparatus for testing the adhesive strength of overlays attached to the inside of plain bearing bushings, comprising:
    a pin mounted rotatably in a pin receptacle and on which there is arranged a first drive mechanism,
    a bushing receptacle, in which the plain bearing bushing to be tested may be fitted, wherein the pin is mounted along an axis of the plain bearing with predetermined clearance in the plain bearing bushing,
    a mechanism for bending the pin by bringing about oscillating relative movement of the bushing receptacle and pin receptacle perpendicularly to the bushing axis, such that a gap opens between the pin and the plain bearing bushing, into which a liquid medium can flow abruptly, and
    a mechanism for feeding the liquid medium into the gap between the pin and plain bearing bushing.

15. The apparatus of claim 14, wherein the pin receptacle is arranged in stationary manner and the bushing receptacle is connected with a second drive mechanism for bringing about the oscillating movement.

16. The apparatus of claim 15, wherein the stationary receptacle comprises a force gauge.

17. The apparatus of claim 15, wherein the second drive mechanism is a force cylinder.

18. The apparatus of claim 14, wherein the bushing receptacle is arranged in stationary manner and the pin receptacle is connected with a second drive mechanism for bringing about the oscillating movement.

19. The apparatus of claim 18, wherein the stationary receptacle comprises a force gauge.

20. The apparatus of claim 14, wherein the pin is hollow.

21. A method for testing the adhesive strength of overlays attached to the inside of plain bearing bushings, having the following steps:
    specifying clearance between the plain bearing bushing to be tested and an either stationary or rotating and/or oscillating pin extending through the plain bearing bushing,
    feeding a liquid medium into the gap between the plain bearing bushing and the pin,
    oscillating the plain bearing bushing and pin relative to one another perpendicularly to the bushing axis for a given period with a given force, wherein the oscillating is performed by holding the plain bearing stationary and oscillating the pin perpendicular to the bushing axis, and wherein the oscillating includes bending the pin, and
    examining the plain bearing bushing after the load test for damage to the overlay.

* * * * *